US00PP10359P

United States Patent [19]

Kristiansen

[11] Patent Number: Plant 10,359

[45] Date of Patent: Apr. 28, 1998

[54] ASTER PLANT NAMED 'LOKE VIKING'

[75] Inventor: Kell Kristiansen, Årslev, Denmark

[73] Assignee: Asterklubben, Arslev, Denmark

[21] Appl. No.: 772,601

[22] Filed: Dec. 23, 1996

[51] Int. Cl.[6] ..... A01H 5/00

[52] U.S. Cl. ..... Plt./68.1

[58] Field of Search ..... Plt./68.1

*Primary Examiner*—James R. Feyrer
*Assistant Examiner*—Elizabeth C. Kemmerer
*Attorney, Agent, or Firm*—C. A. Whealy

[57] ABSTRACT

A distinct cultivar of Aster plant named 'Loke Viking', characterized by its rapid growth rate and moderate vigor; freely branching and uniform plant habit; very freely flowering even under winter conditions; large daisy-type inflorescences with dark red purple ray florets and yellow centers; and good post-production longevity.

1 Drawing Sheet

The present invention relates to a new and distinct cultivar of pot Aster plant, botanically known as *Aster novi-belgii* and referred to by the cultivar name Loke Viking.

The new cultivar is a product of a planned breeding program conducted by the inventor in Årslev, Denmark. The objective of the breeding program was to create new Aster cultivars having desirable inflorescence colors, uniform plant habit and rapid growth rate.

The new cultivar originated from a cross made in 1994, by the inventor of the cultivar Lilac Lady (not patented) as the male or pollen parent with the cultivar Royal Ruby (not patented) as the female or seed parent.

The cultivar Loke Viking was discovered and selected by the inventor as a flowering plant within the progeny of the stated cross in a controlled environment in Årslev, Denmark. Asexual reproduction of the new cultivar by terminal cuttings taken at Årslev, Denmark, has shown that the unique features of this Aster are stable and reproduced true to type in successive generations of asexual reproduction.

The following traits have been repeatedly observed and are determined to be in unique characteristics of 'Loke Viking'. These characteristics in combination distinguish 'Loke Viking' as a new and distinct cultivar:

1. Rapid growth rate and moderate vigor.
2. Freely branching and uniform plant habit.
3. Very freely flowering even under winter conditions.
4. Large daisy-type inflorescences with dark red purple ray florets and yellow centers.
5. Good post-production longevity.

The cultivar Loke Viking has not been observed under all possible environmental conditions. The phenotype may vary somewhat with variations in environment such as temperature, daylength and light intensity, without, however, any variance in genotype.

In comparison to plants of the new Aster, plants of the male parent, the cultivar Lilac Lady, are taller and differ in ray floret color. In comparison to plants of the new Aster, plants of the female parent, the cultivar Royal Ruby, have lighter-colored ray florets and poor postproduction longevity.

The accompanying colored photographs illustrate the overall appearance of the new cultivar, showing the colors as true as it is reasonably possible to obtain in colored reproduction of this type.

The first photograph comprises a top perspective view of typical flowering plant of the new Aster.

The second photograph comprises a top perspective view of a typical inflorescence of the new Aster. Floret and foliage colors in these photographs may vary from the actual ray and foliage colors due to light reflectance.

In the following description, color references are made to The Royal Horticultural Society Colour Chart except where general terms of ordinary dictionary significance are used. The following observations and measurements describe plants grown in Årslev, Denmark, under glass with average day and night temperatures of 20C. Plants received long day/short night treatments for the first six weeks, then short day/long night until flowering. Measurements and numerical values represent ranges or averages for six typical flowering plants.

Botanical classification: *Aster novi-belgii* cultivar Loke Viking.

Commercial classification: Pot Aster.

Parentage:

*Male or pollen parent.*—*Aster novi-belgii* Lilac Lady (not patented).

*Female or seed parent.*—*Aster novi-belgii* Royal Ruby (not patented).

Propagation:

*Type.*—Terminal tip cuttings.

*Time to rooting.*—Summer: About 12 days at a temperature of 21C. Winter: About 13 days at a temperature of 21C.

*Rooting habit.*—fine, fibrous and well-branched.

Plant description:

*Appearance.*—Perennial herbaceous decorative container plant. Stems upright to outward, inverted triangle, uniform habit and very freely branching. Rapid growth rate and moderate vigor. Appropriate for 10 to 15-cm containers. Usually about 11 weeks are required to produce a flowering plant.

*Plant height.*—13 to 16 cm.

*Plant width.*—25 to 30 cm.

*Stem diameter.*—2 to 5 mm.

*Foliage description.*—Arrangement: Distichous. Shape: Elliptic with acute apex and auriculate base, margin entire. Size: Length: 3.5 to 5.5 cm. Width: 1 to 2 cm. Texture: Glabrous, leathery. Color: Abaxial surface: 137A. Adaxial surface: 137C.

Flowering description:

*Appearance.*—Daisy inflorescence form. Flat inflorescences borne on terminals above foliage, arising from leaf axils. Disc and ray florets arranged acropetally on a capitulum.

*Flowering response.*—Under natural conditions, plant flower in the late summer/autumn in the Northern Hemisphere. At other times of the year, inflorescence initiation and development can be induced under short day/long night conditions.

*Post-production longevity.*—Good, inflorescences last about three to four weeks on the plant. Inflorescences persistent.

*Quantity of inflorescences.*—Inflorescences form at every leaf axil. Very freely flowering, usually 8 to 12 inflorescences per flowering stem.

*Inflorescence size.*—Diameter: 3 to 3.5 cm. Depth (height): 1 to 1.5 cm. Diameter of disc: 1 to 1.2 cm.

*Bud.*—Shape: Ovoid. Size: Length: 8 to 10 mm. Diameter: 6 to 8 mm.

*Ray florets.*—Quantity: 50 to 150 per inflorescence. Number of whorls: More than two. Shape: Narrowly obovate to tubular, with obtuse apex and entire margin. Size: Length: 2.5 to 2.8 cm. Width: 1 to 3 mm. Texture: Satiny, smooth and glabrous. Aspect: Flat to concave. Orientation: Horizontal to peduncle. Color: Mature, abaxial surface: 72B to 71A. Mature, adaxial surface: 78B.

*Disc florets.*—Quantity: 30 to 45 per inflorescence. Shape: Funnel. Length: 5 to 7 mm. Color, apex of corolla: Immature: Purple. Mature: Nearly transparent.

*Peduncle.*—Aspect: Angled about 45° to the stem. Length: 2 to 3 cm. Texture: Glabrous. Color: 137A.

*Reproductive organs.*—Androecium: Present on disc florets only. Anther positions: Even with apex of disc corolla. Anther size: About 1 mm. Anther color: 14B. Pollen: Moderate, 14B in color. Gynoecium: Present on both ray and disc florets. Stigma position: Above the anthers. Stigma shape: Bifurcate. Stigma color: 4D.

Disease resistance: No known Aster diseases observed to date on plants grown under commercial greenhouse conditions.

Seed production: Seed production has not been observed.

It is claimed:

1. A new and distinct cultivar of Aster plant named 'Loke Viking', as illustrated and described.

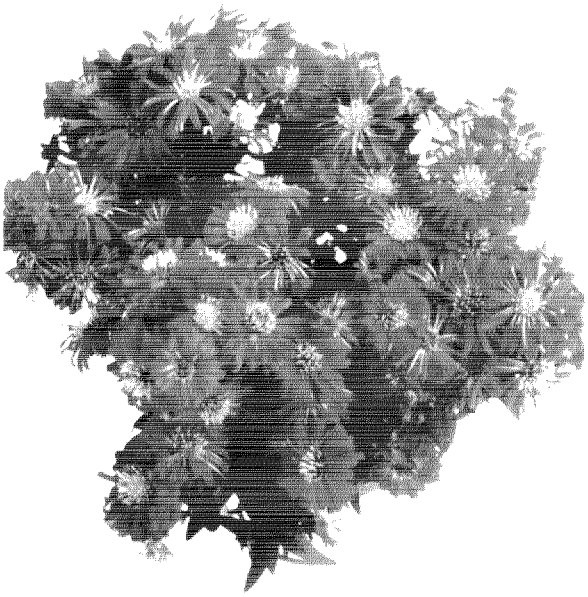
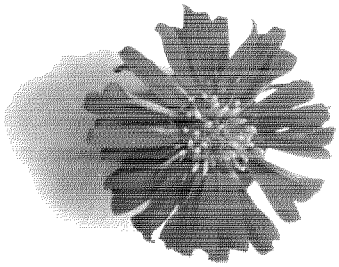

* * * * *